(12) United States Patent
Kraahs et al.

(10) Patent No.: US 8,481,060 B2
(45) Date of Patent: Jul. 9, 2013

(54) MELT-COATED PHARMACEUTICAL COMPOSITION WITH FAST RELEASE

(75) Inventors: Peter Kraahs, Bad Krozingen (DE); Stefanie Bold, Muellheim (DE); Lars Fahsel, Niederndodeleben (DE)

(73) Assignee: Losan Pharma GmbH, Neuenburg (DE)

( * ) Notice: Subject to any disclaimer, the term of this patent is extended or adjusted under 35 U.S.C. 154(b) by 0 days.

(21) Appl. No.: 13/140,585

(22) PCT Filed: Dec. 17, 2009

(86) PCT No.: PCT/EP2009/067371
§ 371 (c)(1),
(2), (4) Date: Jun. 17, 2011

(87) PCT Pub. No.: WO2010/070028
PCT Pub. Date: Jun. 24, 2010

(65) Prior Publication Data
US 2011/0250244 A1    Oct. 13, 2011

(30) Foreign Application Priority Data

Dec. 17, 2008   (EP) .................................... 08021917

(51) Int. Cl.
*A61K 9/00*      (2006.01)
*A61K 31/341*    (2006.01)
*A61K 31/522*    (2006.01)
*A61K 31/167*    (2006.01)

(52) U.S. Cl.
USPC ...... 424/400; 514/630; 514/471; 514/263.34; 427/2.21

(58) Field of Classification Search
USPC ...... 424/400; 514/630, 471, 263.34; 427/2.21
See application file for complete search history.

(56) References Cited

U.S. PATENT DOCUMENTS 4,948,622 A * 8/1990 Kokubo et al. .............. 427/2.16
5,270,055 A    12/1993 Moest

FOREIGN PATENT DOCUMENTS

| EP | 1891936 A1 | 8/2006 |
| WO | WO 2004/103350 A | 12/2004 |
| WO | WO 2005/063203 A | 7/2005 |
| WO | WO 2009/005613 A | 1/2009 |

* cited by examiner

*Primary Examiner* — Aradhana Sasan
(74) *Attorney, Agent, or Firm* — Chalin A. Smith; Smith Patent Consulting

(57) ABSTRACT

The present invention relates to a process for producing a solid, coated pharmaceutical composition by a melt coating process. The process is adapted to provide a solid, coated pharmaceutical composition by melt coating, which has a fast release.

19 Claims, No Drawings

MELT-COATED PHARMACEUTICAL COMPOSITION WITH FAST RELEASE

This application corresponds to the national phase of International Application No. PCT/EP2009/067371 filed Dec. 17, 2009, which, in turn, claims priority to European Patent Application No. 08.021917.3 filed Dec. 17, 2008, the contents of which are incorporated by reference herein in their entirety.

The present invention relates to a process for producing a solid, coated pharmaceutical composition by a hot-melt coating process. The process is adapted to provide a solid, coated pharmaceutical composition by hot-melt coating, which has a fast release.

Many pharmaceutically active ingredients have a bitter and/or unpleasant taste, and when providing a solid, oral composition of such an active ingredient, it is advantageous to provide the solid, oral pharmaceutical composition with a coating to mask the bitter and/or unpleasant taste of the active ingredient (taste-masking). A typical example of such an active ingredient is acetaminophen, but other active ingredients having this challenge are known as well.

In the prior art processes for coating solid, pharmaceutical compositions having an unpleasant or bitter taste have been known for a long time. In such a coating process the solid pharmaceutical composition is provided with a layer that covers the unpleasant-tasting core with the pharmaceutically active ingredient. This layer masks the unpleasant taste of the core of the pharmaceutical composition in the mouth and dissolves in the gastrointestinal tract. Such layers are generally referred to as taste-masking layers or taste-masking coatings.

Early examples of coating techniques to provide such a taste-masking layer are sugar coatings which provide a sugar layer that covers the unpleasant tasting core of the pharmaceutical composition. In more recent times, other coating techniques became available. Today, the probably most widely spread technique is providing a coating solution or suspension of a coating polymer in an organic or preferably aqueous solvent. This coating solution or suspension is applied onto the unpleasant tasting core of the pharmaceutical composition and the solvent is evaporated, so that the taste-masking polymer and optionally additives remain in the taste-masking layer. This process, however, has the disadvantage that it is rather energy consuming, as the solvent of the coating composition must be evaporated. This is generally easy and can be done at low temperatures, if the solvent is an organic solvent, however, great care must be taken that as little as possible organic solvent remains in the coating for safety reasons. Coating compositions on water basis are not problematic regarding the residues of the coating solvent, as water does not pose a problem in pharmaceutical compositions, however, many active ingredients are susceptible to water, and furthermore, removing water from the taste-masking layer after the layer has been applied is energy- and time-consuming. Despite these problems, today aqueous coating techniques are most common, because there is an apparent lack of alternatives.

An alternative coating technique is the hot-melt coating technique. This technique has also been known for a long time, and instead of a coating solution or suspension in which the components of the coating layer are dissolved or suspended in an organic or aqueous solvent in the hot-melt coating process a melt is provided at a temperature at which the taste-masking compound is in the molten phase. As moldable taste-masking substance mainly lipophilic compounds are used, such as lipids, triglycerides, partial glycerides, waxes, glyceride fatty alcohol ethers etc. The melt optionally contains additives of the taste-masking layer either in suspension or in solution. The melt is then sprayed onto the cores of the pharmaceutical composition containing the unpleasant or bitter-tasting pharmaceutically active ingredient.

This method is advantageous, as no solvent is involved that later has to be removed or that can react with components of the core of the pharmaceutical composition. However, applying a taste-masking layer by spray-coating the core of a pharmaceutical composition with a melt of the predominantly lipophilic taste-masking compound leads to pharmaceutical compositions in which the release of the active ingredient from the core of the pharmaceutical composition is significantly delayed. This is described in several scientific articles, e.g. in Barthelemy, P.; Laforet, J. P.; Farah, N.; Joachim, J.: Compritol 888 ATO: an innovative hot-melt coating agent for prolonged-release drug formulations, Eur J. Pharm. Biopharm. 47, 1 (1999), 87-90, Sinchaipanid, N.; Junyaprasert, V; Mitrevej, A; Application of hot-melt coating for controlled release of propanol hydrochloride pellets, Powder Technol. 141 (2004), 203-209 and Joachim, J.; Prinderre, P.; Farah, N.; A Hot Melt Coating Agent for Controlled-Release Theophylline Dosage Forms, Pharm. Man. Rev. (1996), 24-28.

Because of these inherent problems with taste-masking layers applied by the hot-melt coating process, this process was considered as not suitable for preparing fast-dissolving pharmaceutical compositions. The process was used for the preparation of sustained-release pharmaceutical compositions, as e.g. described in EP 1 479 383 and the articles mentioned above.

WO 2005/063203 discloses that it is difficult to provide a melt coated pharmaceutical composition that has fast release of the active ingredient and wherein the coat completely covers the core with the active ingredient. Thus, this document discloses a melt coating process in which the molten taste-masking material is not sprayed onto the core with the active ingredient. Rather the taste-masking compound is mixed with the core and then molten. The document suggests using taste-masking materials such as xylitol having a high HLB-value, i.e. being hydrophilic. The possibility to influence the integrity of the taste-masking layer is not disclosed in WO 2005/063203.

WO 2004/103350 discloses sustained release compositions of the active ingredient beraprost sodium which comprise a sustained release layer and a taste-masking layer. There is no disclosure in this document how the taste-masking layer is applied and because the document relates to a controlled release formulation, it is not disclosed to manipulate the taste-masking layer to increase the release of the active ingredient.

EP 0 841 062 discloses a variation of a melt coating process in which granules are prepared by melt granulation. These granules are then layered with talc and, optionally, ethyl cellulose, and the granules are molten again. By this process a kind of layer containing talc and ethyl cellulose is formed on the surface of the granules, which provides some taste-masking combined with only a small effect on the release. The process disclosed in EP 0 841 062 is not a "classic" hot-melt coating process, in which the taste-masking compound is molten and then sprayed onto a core of a pharmaceutical composition. The process of EP 0 841 062 does not exclude that pharmaceutically active ingredient is present in the outermost layer of the pharmaceutical composition, as it does not provide a layer of a taste-masking compound around the core with the active ingredient. Furthermore, this process disclosed in EP 0 841 062 is restricted to cores which can be molten and thus to pharmaceutically active ingredients which can be used in such preparations. It is furthermore not possible to carry out this process in standard commercially available coating apparatus.

There exists a need in the art for a process for providing pharmaceutical compositions with a taste-masking layer that is generally applicable to all kinds of pharmaceutical compositions and that provides pharmaceutical compositions, in which the release of the active ingredient is not significantly delayed, that is safe and economical and avoids the problems of the prior art processes. There is also a need for pharmaceutical compositions obtained by such a process.

The present inventors now found that a process for producing a solid, coated pharmaceutical composition comprising
 (i) providing a core containing one or more pharmaceutically active ingredients and optionally one or more pharmaceutically acceptable excipients,
 (ii) spray-coating the core with at least one coating composition comprising at least one taste-masking compound having a melting point of at least 40° C. and an HLB value of 10 or less, wherein the at least one coating composition comprising the taste-masking compound has a temperature of at least 40° C. when it is sprayed onto the core, so that the taste-masking compound is in the melt phase, whereby a taste-masking layer is provided onto the core,
characterized in that the core is spray-coated with at least one coating composition comprising at least one release compound which is defined as a compound which in the gastrointestinal tract either causes disruption or disintegration of the taste-masking layer or improves the permeability of the taste-masking layer for the one or more pharmaceutically active ingredients solves these problems.

The present invention also provides solid, coated pharmaceutical compositions obtainable according to such a process.

The process of the present invention is a hot-melt coating process in which a melt is directly sprayed onto the core of a pharmaceutical composition which contains one or more pharmaceutically active ingredients. The melt contains a taste-masking compound in the molten state. The melt, of course, can contain more than one taste-masking compound, and it can contain usual additives known for use in the hot-melt coating process, e.g. for improving the processability of the coating composition. These additives and/or the other taste-masking compounds are either also in the molten state or they are suspended or emulsified in the melt or they are dissolved in the melt. It is preferred that the composition that is used in the present process for spray-coating the core with the one or more pharmaceutically active ingredients contains no solvents. However, it is possible that a small amount of water is present, e.g. for emulsifying the additives. The amount of water present in the composition is preferably in the range of 0 to 20%, more preferably in the range of 0 to 10%. The taste-masking layer is the outermost layer of the pharmaceutical composition.

Decisive for the present invention is the use of a release compound. A release compound according to the present invention is any compound which in the gastrointestinal tract, in particular in the stomach, causes disruption or disintegration of the taste-masking layer or improves the permeability of the taste-masking layer for the one or more pharmaceutically active ingredients that are present in the core of the pharmaceutical composition.

It goes without saying that the release compound is different from the taste-masking compound. Preferred release compounds are selected from the group consisting of
 compounds which react under acidic conditions (e.g. forming carbon dioxide), in particular salts of carbonic acid, such as alkaline carbonates, alkaline hydrogen carbonates, alkaline earth carbonates, alkaline earth hydrogen carbonates and others
 inorganic salts that are soluble in aqueous media (solubility preferably at least 0.5 g salt in 10 ml water or 0.1 n HCl, more preferably at least 1 g salt in 10 ml water or 0.1 n HCl, most preferred at least 10 g salt in 10 ml water or 0.1 n HCl at 20° C.), such as halides (preferably chlorides and bromides) or sulfates such as alkaline halides and sulfates, alkaline earth halides and sulfates (preferred are alkaline halides such as NaCl or KCl).
 swelling agents that significantly increase their volume upon contact with aqueous media, such as starch, polysaccharides and other disintegrating agents, preferably the disintegrating agents known as super disintegrants, in particular crosscarmellose, crosspovidone, sodium starch glycolate, polyacrylic exchange resins, polyacrylic acids, and carbomers,
 hydrophilic polymers which are soluble in aqueous media, such as povidone, polyvinyl alcohol-polyethylene glycol copolymer and cellulose ethers,
 organic compounds that are soluble in aqueous media (solubility as defined above for the inorganic salts), such as carbohydrates, such as sucrose, glucose, lactose, mannitol, maltitol and sorbitol.

As used in the present specification, the term "aqueous media" means water or aqueous solutions or suspensions with a pH value in the range of 0.5 to 8. The term "aqueous media" particularly encompasses the media that are found in the gastrointestinal tract of humans. The term "aqueous medium" in particular means water and 0.1 m HCl.

Which release compounds are preferred depends on the structure of the pharmaceutical composition as will be explained in the following, but in general, most preferred are the compounds which react under acidic conditions, inorganic salts that are soluble in aqueous media and the swelling agents as defined above.

In the following description, for the sake of conciseness, it will sometimes be referred to "the pharmaceutically active ingredient"; it should be understood that this is not a restriction to only one pharmaceutically active ingredient but that always one more pharmaceutically active ingredients are meant, if nothing else is explicitly stated or obvious in the context.

According to the invention it is preferred that the release compound is in the same layer as the taste-masking compound. This can either be achieved by including the release compound into the coating composition containing the molten taste-masking compound. Alternatively, the coating composition containing the molten taste-masking compound and the release compound are simultaneously sprayed onto the core of the pharmaceutical composition containing the pharmaceutically active ingredient. If the release compound is sprayed simultaneously with the melt of the taste-masking compound, the release compound can be sprayed as such (e.g. as a powder) or it can also be sprayed as a melt, generally as a suspension or solution of the release compound in a molten compound (e.g. the taste-masking compound). Preferred is the embodiment, wherein the release compound is either included in the coating composition containing the taste-masking compound and the embodiment, wherein the release compound is directly sprayed (as a powder) onto the core containing the pharmaceutically active ingredient simultaneously with the coating composition comprising the molten taste-masking compound.

In the above embodiment, wherein the release compound is present in the taste-masking layer, it is preferred that the release compound is a compound which reacts under acidic conditions or a swelling agent, and most preferred are basic inorganic salts of carbonic acid as defined above, such as sodium carbonate, sodium bicarbonate, potassium carbonate, potassium bicarbonate or mixtures of those or swelling agents as defined above, such as starch, crosscarmellose, crosspovidone, sodium starch glycolate, polyacrylic exchange resins, polyacrylic acids, carbomers and polysaccharides or mixtures of those. In the gastrointestinal tract, in particular together with the acid in the stomach, the carbonic acid salt that is present in the taste-masking layer will react with the acid and form holes in the taste-masking layer or preferably disrupt and destroy the taste-masking layer. This occurs very fast, and thus the release of the active ingredient from the pharmaceutical composition is not or only minimally delayed by the hot-melt coated taste-masking layer.

The compounds which react under acidic conditions can also be organic compounds, however, the use of carbonic acid salts as release compounds is preferred. The amount of the compounds which react under acidic conditions is not particularly restricted and can easily be adapted by a skilled person depending on the type of taste-masking compound, the thickness of the taste-masking layer, the type of the compound which reacts under acidic conditions, etc. Generally, the amount of the release compound which reacts under acidic conditions (in particular of the carbonic acid salts, such as the inorganic carbonates or hydrogen carbonates) is in the range of 5 to 50%, based on the weight of the coating composition, more preferably in the range of 5 to 40%, more preferably in the range of 5 to 35%, most preferably in the range of 5 to 25%.

It is also possible that the release compound is an inorganic salt or an organic compound or a hydrophilic polymer that is soluble in aqueous media and dissolves in the taste-masking layer, when the pharmaceutical composition reaches the gastrointestinal tract (i.e. the stomach or the intestine). Suitable inorganic salts are e.g. sodium chloride, potassium chloride, etc. The inorganic salts are preferably inorganic salts having a solubility in water and/or acid as defined above. When the pharmaceutical composition with the taste-masking layer containing the compound that is soluble in aqueous media reaches the gastrointestinal tract, the compound is dissolved and provides pores in the taste-masking layer. The active ingredient can then pass the taste-masking layer through these pores, which leads to a fast release of the active ingredient. However, the release tends to be somewhat more delayed than in the embodiment, where a compound which reacts under acidic conditions is present in the taste-masking layer, and thus the embodiment in which a compound which reacts under acidic conditions is present in the taste-masking layer is preferred.

It is understood that some compounds which react under acidic conditions as defined above are also soluble in aqueous media. However, for the purpose of this specification, a compound that meets the requirements of a compound which reacts under acidic conditions is not considered as belonging to the inorganic salt or organic compounds or hydrophilic polymers that are soluble in aqueous media as defined above.

The amount of inorganic salt or organic compounds or hydrophilic polymers that are soluble in aqueous media in the taste-masking layer is not particularly restricted, and the same amount can be used as explained above with respect to the compounds which react under acidic conditions. The inorganic salts or organic compounds or hydrophilic polymers that are soluble in aqueous media can be applied onto the core containing the pharmaceutically active ingredient in essentially the same way as the compound which reacts under acidic conditions, and it is referred to the corresponding explanations above.

Examples of an organic compound that is soluble in aqueous media are sucrose, glucose, lactose, sorbitol, mannitol, xylitol maltitol, isomalt, dextrose, fructose or salts of organic acids. However, inorganic salts that are soluble in aqueous media are preferred.

In a third embodiment the release compound can be a compound that swells in an aqueous medium and thus disrupts or disintegrates the taste-masking layer, when the taste-masking layer reaches an aqueous, in particular an acidic environment. The usual well-known and pharmaceutically acceptable swelling agents and disintegrating agents, such as starch, e.g. maize starch and pregelatinized starch, polysaccharides and the super disintegrants, such as crosscarmellose, crosspovidone, sodium starch glycolate, polyacrylic acids, carbomers and polyacrylic exchange resins are preferred swelling agents.

The amount of swellable compound in the coating composition is not particularly restricted and can easily be adjusted by a skilled person based on the same considerations explained above in connection with the compounds which react under acidic conditions. The amount of swellable compound in the coating composition is preferably in the same ranges as disclosed above in connection with the compounds which react under acidic conditions. The swellable compounds can be applied in the same manner as discussed above, i.e. as components of the coating composition containing the taste-masking compound, or they can be sprayed onto the core simultaneously with the taste-masking composition as such, or they can be applied also in melt form.

If the release compound is a compound which reacts under acidic conditions, in particular a carbonic acid salt, such as an inorganic carbonate or hydrogen carbonate (most preferred embodiment), the disruption, disintegration (or hole-forming) in the taste-masking layer essentially starts when the pharmaceutical composition reaches the acidic environment of the stomach. Therefore, this embodiment is most preferred. The pharmaceutical composition can be left in the mouth for a long time without the active ingredient bleaching out and providing a bitter taste in the mouth. Some dissolution of the compound which reacts under acidic conditions may occur in the mouth, but this usually is negligible.

With the other two embodiments discussed above in which the release compound is an inorganic salt or organic compound or hydrophilic polymer that is soluble in aqueous media or a swelling agent, the process in which pores are formed in the taste-masking layer or in which swelling occurs in the taste-masking layer may already occur in the mouth. Therefore, the taste-masking layer might be thicker as in the case of compounds which react under acidic conditions and in those embodiments there may be some delay in the release of the active ingredient. Nevertheless, the release of the active ingredient is significantly improved over embodiments of the prior art which do not comprise a release compound. For this reason, the embodiment in which the release compound is a compound which reacts under acidic conditions, in particular an inorganic carbonate or hydrogen carbonate, is particularly preferred.

Above, embodiments of the invention have been explained in which the release compound is present in the same layer as the taste-masking compound. It is, however, also possible to provide a separate layer containing the release compound. In this embodiment, a core containing the pharmaceutically active compound is first coated with a layer containing the release compound, and on this layer the taste-masking layer is applied by hot-melt coating (of course, it is also possible but not preferred to separate the layer with the release compound from the layer with the taste-masking compound by one or more intermediate layers; preferably, there is no intermediate layer between the taste-masking layer and the release layer). The release layer can be applied by any known method, but generally, a hot-melt coating process will also be used for applying the release layer for economic reasons. In this embodiment the release compound is particularly preferred a compound which reacts under acidic conditions as defined above or a swelling compound as defined above, because the release layer must be able to disrupt or disintegrate the taste-masking layer when some small amounts of water or acid penetrate the taste-masking layer and reach the release layer. Regarding the preferred embodiments of the release layer, it can be referred to the disclosure above in which the embodiment of the present invention is described, in which the release compound is present in the taste-masking layer.

It is, of course, also possible to use a separate release layer and a separate taste-masking layer and to provide a release compound also in the taste-masking layer. In this case, small amounts of water or acid in the gastrointestinal tract can more easily reach the release layer, and the disruption or disintegration of the taste-masking layer by disrupting or disintegrating the release layer is improved. In this embodiment the amount of release compound in the taste-masking layer might be much lower than discussed above for the embodiments in which no separate release layer is present, and in this case the amount of release compound in the taste-masking layer is generally 0.5% or more, more preferably 1% or more but generally not higher than 10%, preferably not higher than 8%, based on the total weight of the composition.

Taste-masking compounds that can be applied by the hot-melt coating process are well-known in the art, and in principle, all taste-masking compounds that are known in the prior art as being useful for providing a taste-masking layer by the hot-melt coating process can be used in the present invention. The taste-masking compounds that can be used in the hot-melt coating process generally have a melting point of more than 40° C., preferably more than 50° C., and the melting point is generally not higher than 100° C., preferably not higher than 90° C., and most preferably not higher than 80° C. The melting point of pharmaceutically acceptable excipients including taste-masking compounds is usually stated in the European Pharmacopoeia, and if the European Pharmacopoeia contains a melting point for a taste-masking compound, this is the melting point referred to in this specification. If the European Pharmacopoeia for some compound does not contain a specific melting point but discloses a method for determining the melting point, this method is to be followed. If no melting point and no specific method is disclosed in the Pharmacopoeia or if the method referred to in the European Pharmacopoeia is not sufficiently clear or complete, the melting point is determined by DSC as follows: The melting point is measured by DSC7 type differential scanning calorimeter (manufactured by Perkin Elmar Inc.) according to the method wherein the sample is heated from room temperature at a heat elevation rate of 30° C./minute up to 150° C. (or the maximum temperature possible before the sample disintegrates), maintained at the same temperature for 10 minutes, then depressed in temperature at a rate of −20° C./minute down to −20° C., maintained at the same temperature for 10 minutes and again heated at a rate of 20° C./minute, whereby a temperature showing a peak of melting is determined as melting point (TM). A sample of 5 mg is used.

A skilled person will understand that many taste-masking compounds do not have a well-defined melting point but have a melt range. For example, the commercial compound Compritol 888 ATO melts in the range of 68° C. to 73° C. If a taste-masking compound does not have a well-defined melting point but a melting range, the upper limit of the melting range of the taste-masking compound must be within the limit as stated above (at least 40° C., etc.).

The taste-masking compounds that are generally used in hot-melt coating processes are lipophilic compounds and the lipophilicity of a compound can be expressed by its HLB value determined according to Griffin (Griffin, W. C.: Classification of surface active agents by HLB, J. Soc. Cosmet. Chem. 1, 1949). Accordingly, the taste-masking compounds generally have an HLB value of 10 or less, more preferably 8 or less and most preferred 5 or less. The HLB value is calculated or measured according to standard procedure as described e.g. in Fiedler, Lexikon der Hilfsstoffe, Editio Cantor Verlag, 5. Aufl., 2002, or, if Fiedler does not provide sufficient information, according to Griffin as mentioned above.

The preferred taste-masking compounds of the present invention are the same taste-masking compounds that have been used in the prior art and are selected from the group consisting of fatty acids, fatty alcohols, fatty acid triglycerides, fatty acid partial glycerides, fatty alcohol-PEG-ethers, fatty alcohol-PEG-esters, fatty acid esters, fatty acid polyglycerols and mixtures thereof. Such taste-masking compounds are commercially available. Preferred taste-masking compounds are stearic acid, saturated polyglycolyzed glycerides, glycerol palmitostearate and glycerol behenate. Most preferred are fatty acids and fatty alcohols, and regarding the definitions of fatty acids and fatty alcohols, it can be referred to Römpp Chemielexikon, 10th edition, catchwords "Fettalkohole" and "Fettsäuren". Of course, from the fatty alcohols and the fatty acids only those are suitable which have the required melting point and HLB value such as 1-nonadecanole, 1-eicosanole, heneicosanole and 1-docosanole. Of the fatty acids stearic acid [melting point 67° C., HLB −6) is particularly preferred, but similar fatty acids, such as nonadecane acid (melting point 69° C., HLB −6), arachinic acid (melting point 75° C., HLB −7), behenic acid (melting point 80° C., HLB −8), palmitinic acid (melting point 63° C., HLB −5), margaric acid (melting point 62° C., HLB −6), etc. are also preferred.

Particularly preferred are also triglycerides and partial glycerides.

The core containing the one or more pharmaceutically active ingredients and optionally one or more pharmaceutically acceptable excipients that is spray-coated according to the present invention is not particularly restricted. All types of cores can be used including crystals of the active ingredient as such, granules, pellets, tablets, capsules etc. Generally, the core contains at least one active ingredient and one or more pharmaceutically acceptable excipients but e.g. in case of crystals of the pure active ingredient, it is not necessary that pharmaceutically acceptable excipients are present. The core can have been prepared by any known method such as melt or wet extrusion, tabletting, roller compaction, granulation, spheronization, layering processes etc. The methods for producing tablet cores are well-known in the prior art, and in this aspect the present invention is not restricted.

The core contains at least one pharmaceutically active ingredient, but it is also possible that mixtures of more than one pharmaceutical ingredient, such as two, three or four pharmaceutically active ingredients are present. Preferably the core contains one or two, most preferably only one pharmaceutically active ingredient.

The type of pharmaceutically active ingredient is not particularly restricted, but the technology is most preferred for pharmaceutically active ingredients that have an unpleasant or bitter taste and therefore need taste-masking to improve their acceptance by the patients. Typical examples of such pharmaceutically active ingredients are acetaminophen, ibuprofen, flurbiprofen, ketoprofen, acetyl salicylic acid, salicylic acid, naproxene, diclofenac, celecoxib, etoricoxib, guaifenesin, dextromethorphan, acetylcystein, cetirizine, loratadine, desloratadine, acemethacin, caffeine, theophylline, chlorphenamine hydrogen maleate, phenylephrine, pseudoephedrine, dihydramine, chlorpheniramine, diphenhydramine, ranitidine, famotidine, cimetidine, loperamide, bisacodyl, ciprofloxacin, norfloxacin, β-lactam antibiotics, macrolide antibiotics.

Ranitidine, famotidine, cimitidine, caffeine, Paracetamol, acetyl salicylic acid (ASA), cetirizine, loratadine, diphenhydramine, gauifenisin, Ibuprofen, ketoprofen, naproxen, acemetacin, pseudoephedrine, phenylephrine, dextromethorphane, calcium acetate, zinc sulfate, zinc fumarate (or zinc salts in general), iron salts, acetyl cysteine, ambroxol, diclofenac, chondroitine, tramadole, tilidine, codeine, azithromycine, clarithromycine, roxythromacine (makrolid antibiotics), beta-lactame antibiotics, triptane (e.g. almo-, nara-, riza-, suma-, zolmi-).

More preferred are the following pharmaceutically active ingredients ranitidine, famotidine, cimitidine, caffeine, paracetamol, acetyl salicylic acid (ASA), cetirizine, loratadine, diphenhydramine, gauifenisin, Ibuprofen, ketoprofen, naproxen, acemetacin, pseudoephedrine, phenylephrine, dextromethorphane, calcium acetate, zinc sulfate, zinc fumarate (or zinc salts in general), iron salts. Particularly preferred are the active ingredients used in the examples of the invention, namely ranitidine, caffeine, Paracetamol and acemetacine. More preferred are Paracetamol, ranitidine and caffeine.

The term "pharmaceutically active ingredients" as used in the present invention also includes vitamins and herbal drugs which very often need taste-masking.

The core also generally contains pharmaceutically acceptable excipients, depending on which type of core is used. However, the core can also consist of a crystal of the active ingredient.

Most preferred according to the present invention is a process in which a core containing one or more (preferably one) pharmaceutically active ingredients and optionally one or more pharmaceutically acceptable excipients is spray-coated with a coating composition comprising at least one (preferably one) taste-masking compound having a melting point of at least 40° C. and an HLB value of 10 or less wherein the coating composition comprising the taste-masking compound has a temperature of at least 40° C. when it is sprayed onto the core, whereby a taste-masking layer is provided onto the core, characterized in that the core is spray-coated with a coating composition comprising at least one release compound (preferably one release compound) which in the gastrointestinal tract either causes disruption of the taste-masking layer or improves the permeability of the taste-masking layer for the one or more pharmaceutically active ingredients. Most preferably there is one layer comprising both the release compound and the taste-masking compound.

The coating composition comprising the at least one release compound that is used in the process of the present invention may also preferably contain one or more further components, e.g. to achieve a homogenous distribution of the release compound. The one or more further components which assist in achieving a homogeneous distribution of the release compound in the layer containing the release compound are designated "additional compounds" in this specification. It is to be understood that the coating composition containing the at least one release compound preferably also contains the at least one taste-masking compound as explained above. Most release compounds are not soluble in the melt that is used in the hot-melt coating process, and therefore, one or more additional compounds are generally used in order to provide an advantageous distribution of the release compound in the coating composition and to prevent segregation during the coating process. The additional compound is preferably selected from the group of surfactants, polyethylene glycols, glycerol and propylene glycol. The surfactant is preferably selected from the group consisting of sorbitane fatty acid esters, polyoxyethylene alkyl ethers, polyoxyethylene castor oil derivatives, polyoxyethylene sorbitane fatty acid esters, polyoxyethylene stearates, polyoxyethylene-polyoxypropylene-copolymers.

The additional compound as defined above can of course also be present in the layer containing the taste-masking compound, if the taste-masking compound is not in the same layer as the release compound.

The amount of the additional compound or compounds as defined above is not particularly limited and can be adapted by a skilled person depending on the identity of the additional compound or compounds and the composition of the coating composition, in particular of the release agent. Generally, the additional compounds are present in the coating composition in an amount of up to 40%, based on the weight of the coating composition, preferably in the range of up to 35%, more preferably of up to 30%, and preferably at least 0.5, 1 or 2% of the additional compound are present.

According to the present invention "%" means "wt.-%", if nothing else is stated or obvious.

The coating composition containing the at least one taste-masking compound can exclusively consist of the taste-masking compound (if the release compound is present in a separate layer), but preferably the release compound and optionally other additives are present in the coating composition that contains the at least one taste masking compound. Thus, preferably the taste-masking compound is present in the coating composition in an amount in the range of 30 to 100%, more preferably of 35 to 90%, most preferably of 40 to 70%, based on the weight of the coating composition.

Additives that can be included into the hot-melt coating composition containing the taste-masking compound and/or the release compound are e.g. coloring agents, pigments, sweeteners or flavors.

The process of the present invention corresponds to a usual hot-melt spray-coating process, except that a release compound is also present in the hot-melt coating composition or applied separately. Regarding details of the hot-melt spray-coating process, it can be referred to the textbook Multiparticulate oral drug delivery (Drugs and the pharmaceutical sciences, Vol. 65), 1994, edited by Isaac Gebhre Sellassie, which insofar as it describes the hot-melt spray-coating process is included herein by reference.

In the hot-melt spray-coating process the hot-melt coating composition containing the taste-masking compound is heated to a temperature at which the taste-masking compound is in a molten state. This is generally at a temperature which is above the melt temperature of the taste-masking compound, however, depending on the composition of the hot-melt coating composition, it is possible that the melt temperature of the composition is somewhat lower than the melt temperature of each of its components, including the taste-masking compound (reduction in melt temperature). Preferably, according to the invention the temperature of the hot melt coating composition containing the taste-masking compound is at least 40° C. and preferably at least the melt temperature of the taste-masking compound, more preferably at least 5° C., more preferably at least 10° C. above the melt temperature of the taste-masking compound. Depending on the apparatus, higher temperatures might be recommended.

The taste-masking coating composition, i.e. the melt containing the molten taste-masking compound and optionally other components, such as the release compound, additional compounds, additives, etc., is then directly sprayed onto the core containing the pharmaceutically active ingredient. The melt becomes solid on the surface of the cores due to the cool process air temperature and the low product temperature and the taste-masking layer is formed. This is contrary to the usual spray-coating process of a solution or suspension, wherein the spraying solution or suspension is applied at a low temperature (generally room temperature) and only the process temperature is high to evaporate the solvent.

The present invention is also directed to the solid, oral pharmaceutical compositions obtainable by the processes as described above. The solid, oral pharmaceutical compositions are different from compositions that were not prepared by the hot-melt coating process, because the taste-masking layer is structurally different, if it has been applied by the hot-melt coating process and not by a solution or suspension process. Furthermore, the taste-masking compounds used in the hot-melt process are generally not usable in a solution or suspension process, and the taste-masking compounds applied by solution and suspension processes do not have a melting point of more than 40° C. in combination with an HLB value of 10 or less. Furthermore, the pharmaceutical compositions of the present invention do not contain any residues of solvent in the taste-masking layer, which is unavoidable in those pharmaceutical compositions which were coated by a solution or suspension process.

The solid, oral pharmaceutical compositions obtainable according to the process of the present invention differ from the known pharmaceutical compositions that have a taste-masking layer prepared by a conventional hot-melt coating process in that the pharmaceutical compositions of the present invention contain a release compound either in the taste-masking layer or as a separate layer.

Compared to pharmaceutical compositions of the prior art that have been prepared by the hot-melt coating process, the pharmaceutical compositions of the present invention have a significantly improved dissolution profile. The dissolution profile is measured according to the paddle method of the European Pharmacopoeia at 75 rpm in 900 ml aqueous buffer (pH between 1 and 7.2, depending on the solubility of the active ingredient) at 37° C. with the following additional provisions. It can also be referred to the examples for further details.

If the release compound is a compound which reacts under acidic conditions, the dissolution profile is first measured under acidic conditions (pH=1) for 30 minutes according to the European Pharmacopoeia. After this initial 30 minutes, the dissolution profile is measured under a pH value at which the active ingredient (or the active ingredients) is soluble.

In all other embodiments, the dissolution profile is measured at a pH value at which the active ingredient (or the active ingredients) is soluble according to the European Pharmacopoeia.

All dissolution measurements are carried out at 37° C. in a USP paddle apparatus type 2. If for a certain active ingredient specific conditions are stipulated in the European Pharmacopoeia, such conditions should be used. If no conditions are stipulated in the European Pharmacopoeia, the above conditions are used. If nothing else is obvious or necessary, a suitable buffer system is used to maintain the pH at the required value. Preferred are phosphor buffers.

Using the experimental protocol as described above, after 45 minutes, preferably at least 50% of the active ingredient, more preferably at least 60% of the active ingredient, more preferably at least 70% of the active ingredient, most preferred at least 75% of the active ingredient and still more preferred at least 85% of the active ingredient are dissolved.

Preferably after 30 minutes at least 40%, more preferably at least 50%, more preferably at least 60%, more preferably at least 70%, more preferably at least 80%, most preferably at least 90% of the active ingredient are dissolved.

The hot-melt-coated pharmaceutical compositions of the present invention release the pharmaceutically active ingredient significantly faster than corresponding compositions which are identical to the pharmaceutical compositions of the present invention with the exception that they do not contain the release compound. A significantly faster release means that after 45 minutes preferably at least 10%, more preferably at least 15%, more preferably at least 20 and more preferably at least 25% more active ingredient are dissolved. For example, if a pharmaceutical composition obtained by the hot-melt coating process having a taste-masking layer with no release compound (prior art composition) after 45 minutes releases 15% of the active ingredient, the release of the active ingredient after 45 minutes according to the present invention (same composition as above but with release compound) is preferably at least 25%, more preferably at least 30%, more preferably at least 35% and most preferably at least 40%. The release of the active ingredient (i.e. the dissolution of the active ingredient) is measured as explained above. However, generally the present invention provides even much faster release than stated above.

The following examples explain the invention in more detail, however, the present invention is not restricted to those examples.

EXAMPLE 1

Crystals of acetaminophen were used as core material in the following examples.

Four coating compositions with two different taste-masking compounds were prepared as follows (the weight of the active ingredient for each sample was 250 g).

For samples 1 and 2, 5% and 25% Calcium carbonate, respectively, based on the weight of the coating composition, was mixed with PEG 3000 (10%, based on the weight of the coating composition) or the surfactant Tween 20 (15%, based on the weight of the coating composition). For samples 3 and 4, 15% and 25% Amberlite IRP 88, respectively, based on the weight of the coating composition, was mixed with PEG 3000 in the amount of 10% and 30%, respectively, based on the weight of the coating composition. The mixtures containing PEG were heated under stirring until the PEG was melted and a homogenous suspension was achieved. The sample containing the liquid surfactant Tween 20 was mixed intensively until a homogenous, paste-like suspension was achieved.

The taste-masking compound was added to the release compound/PEG mixture and heated or the mixture of release compound/Tween 20 was added to the melted taste-masking compound. All samples were heated approximately 20° C. above the melting temperature of the taste-masking compound and stirred until a homogenous coating composition was achieved.

The composition of each coating composition is summarized in the following table.

| Sample No. | Release Compound/ Amount | Taste-masking Compound/Amount | Surfactant or other substance/ Amount | Amount of coating (based on the weight of the cores) |
|---|---|---|---|---|
| 1 | CaCO₃/5 g | Precirol ATO 5/85 g | PEG 3000/10 g | 40% |
| 2 | CaCO₃/25 g | stearic acid/60 g | Tween 20/15 g | 40% |
| 3 | Amberlite IRP 88/15 g | stearic acid/75 g | PEG 3000/10 g | 40% |
| 4 | Amberlite IRP 88/25 g | Precirol ATO 5/45 g | PEG 3000/30 g | 40% |

In a fluidized-bed apparatus equipped with a heated nozzle system the crystalline acetaminophen as described above was coated with each of the four coating compositions under the conditions as described below.

The parts of the coating apparatus that were in direct contact with the melted coating composition were heated to avoid solidification of the melt, i.e. the spraying nozzle and the tubes for the transportation of the melt from the melting vessel to the spraying nozzle. The coating compositions were heated to approximately 90° C. to achieve a melt with a low viscosity and satisfying spraying properties.

0.25 kg of the acetaminophen crystals were loaded into the coating apparatus and the crystals were fluidized by the process air stream which was not heated and had a temperature of 20-30° C. The melts were sprayed onto the acetaminophen crystals at a spraying rate of 3 to 8 g/min/0.25 kg cores. The product temperature did not exceed 45° C. over the complete spraying process. After finishing the spraying process the coated cores were kept agitated with the process air stream to cool down and then unloaded.

Simultaneously with spraying each coating composition on the pellets, a release compound was also sprayed as such onto the pellets. The following two release compounds were used in the amount and under the spraying conditions summarized in the following table.

| | | taste masking composition | | Amount of coating |
|---|---|---|---|---|
| Sample No. | Release compound/ Amount | Taste-masking Compound/ Amount | Surfactant or other substance/ Amount | (based on the weight of the cores) |
| 5 | CaCO₃ + 1% Aerosil (based on the weight of CaCO₃)/5 g | Precirol ATO 5/90 g | PEG 3000/10 g | 40% |
| 6 | CaCO₃ + Aerosil (based on the weight of CaCO₃)/25 g | Precirol ATO 5/45 g | PEG 3000/30 g | 40% |

This leads to a total of 6 samples, the composition of which is summarized in the following table:

| Sample No. | Release Compound/ Amount | Taste-masking Compound/ Amount | Surfactant/ Amount | Amount of coating (based on the weight of the cores) |
|---|---|---|---|---|
| 1 | CaCO₃/5 g | Precirol ATO 5/85 g | PEG 3000/10 g | 40% |
| 2 | CaCO₃/25 g % | stearic acid/ 60 g | Tween 20/15 g | 40% |
| 3 | Amberlite IRP 88/15 g | stearic acid/ 75 g | PEG 3000/10 g | 40% |
| 4 | Amberlite IRP 88/25 g | Precirol ATO 5/45 g | PEG 3000/30 g | 40% |
| 5 | CaCO₃ +1 % Aerosil (based on the weight of CaCO₃)/5 g | Precirol ATO 5/90 g | PEG 3000/10 g | 40% |
| 6 | CaCO₃ + 1 % Aerosil (based on the weight of CaCO₃)/25 g | Precirol ATO 5/45 g | PEG 3000/30 g | 40% |

EXAMPLE 2

Following exactly the protocol as described in example 1 above, samples 1 b to 3b have been prepared, which correspond to samples 1 to 4 as described above, but no release compound was sprayed simultaneously with the taste-masking melt coating composition. The compositions of example 2 are summarized in the table below

| Sample No. | Taste-masking Compound/Amount | Surfactant/ Amount | Amount of coating (based on the weight of the cores) |
|---|---|---|---|
| 1b | Precirol ATO 5/71.25 g % | PEG/3.75 g | 30% |
| 2b | stearic acid/63.75 g | PEG/11.27 g | 30% |
| 3b | stearic acid/90 g | Tween 20/10 g | 40% |

EXAMPLE 3

Following exactly the protocol as described in example 1 above, samples 4b to 5b have been prepared, which correspond to samples 1 to 4 as described above, but no release compound and no surfactant or PEG 3000 was sprayed simultaneously with the taste-masking melt coating composition. The compositions of example 3 are summarized in the table below.

| Sample No. | Taste-masking Compound/ Amount | Amount of coating (based on the weight of the cores) |
|---|---|---|
| 4b | Precirol ATO 100 g | 40% |
| 5b | stearic acid 100 g | 40% |

EXAMPLE 4

Each sample obtained in example 1 was subjected to a dissolution experiment according to the European Pharmacopoeia. The protocol of the dissolution measurement was as follows: Dissolution was performed in 900 ml 0.1M HCl at a temperature of 37.0±0.5° C. and a stirrer speed of 75±3 rpm using USP Apparatus 2. The concentration of the dissolved active ingredient was determined by UV-spectroscopy at suitable points in time.

According to the same protocol as disclosed above, the samples obtained in example 2 and 3 were also measured. The results of the dissolution tests are summarized in the following table:

| | Percent active ingredient dissolved | | | | | |
|---|---|---|---|---|---|---|
| Sample No. | 5 min | 10 min | 15 min | 30 min | 45 min | 60 min |
| 1 | 9.3 | 20.2 | 29.7 | 50.6 | 63.7 | 72.3 |
| 1b | 6.4 | 11.7 | 16.1 | 26.6 | 34.4 | 40.4 |
| 2 | 81.0 | 91.9 | 98.0 | 101.5 | — | — |
| 2b | 5.6 | 13.1 | 18.2 | 32.5 | 36.8 | 51.8 |
| 3 | 10.0 | 28.4 | 38.9 | 61.4 | 75.0 | 83.7 |
| 3b | 4.8 | 7.8 | 10.6 | 19.9 | 25.8 | 30.5 |
| 4 | 65.4 | 97.8 | 103.4 | 104.5 | — | — |
| 4b | 2.8 | 4.5 | 6.2 | 10.4 | 14.0 | 17.5 |
| 5 | 7.4 | 13.7 | 23.8 | 44.8 | 58.3 | 66.8 |
| 5b | 0.8 | 1.2 | 1.5 | 2.2 | 2.7 | 3.2 |
| 6 | 62.3 | 78.9 | 91.6 | 100.3 | — | — |

It can be seen that the samples of the present invention, which are the samples of example 1, have a significantly improved release rate compared to comparative samples, which are the samples of example 2 and 3.

EXAMPLE 5

Following the protocol as described in example 1, samples 7 to 31 were prepared. The dissolution properties of these samples were measured following the protocol as described in example 4. The results are summarized in the following table. In the table the abbreviations have the following meaning:

Pre: Precirol ATO 5 (mixture of mono-, di- and triglycerides of palmitic and stearic acid, HLB=2)
Amb: Amberlite (ion-exchange resin)
Cr EL: Cremophor EL (polyethoxylated castor oil)
Cr A6: Cremophor A6 (polyethylene glycol 260 mono(hexadecyl/octadecyl)ether and 1-octadecanol)
Gelu: Gelucire 50/13
PEG: Polyethyleneglycol 4000
Comp Compritol 888 ATO The numbers in parenthesis give the wt.-% amount of the component in the coating:

| Sample No. | taste-masking component | surfactant or other substance | Release compound | active ingredient | percent active ingredient dissolution | | | |
|---|---|---|---|---|---|---|---|---|
| | | | | | 5 min | 15 min | 30 min | 60 min |
| 7 | Pre (85) | Cr A6 (5) | Polyox (10) | Paracetamol | 12.3 | 35.2 | 76.8 | 96.1 |
| 8 | Pre (75) | Labrafil (5) | Polyox (20) | Paracetamol | 7.6 | 38.9 | 79.3 | 92.1 |
| 9 | Comp (73) | Gelu (12) Labrafil (5) | CaCO3 (10) | Paracetamol | 34.9 | 103.2 | 102.8 | 103.6 |
| 10 | Pre (69)) | Gelu (6) (Labrafil (5) | Amb (10), CaCO3 (10) | Paracetamol | 13.2 | 63.5 | 94.5 | 97.3 |
| 11 | Pre (65) | PEG 6000 (15) | Collidon CL-M (20) | Ranitidine HCl | 22.8 | 68.3 | 88.6 | 93.4 |
| 12 | Pre (60) | Cr EL (20) | Carbopol 971P NF (20) | Paracetamol | 38 | 91.6 | 98.9 | 99 |
| 13 | Comp (80) | Cr A6 (5) | CaCO3 (15) | Ranitidine HCl | 16.5 | 62.8 | 84.5 | 93.3 |
| 14 | Pre (70) | Cr EL (20) | Carbopol 971P NF (10) | Ranitidine HCl | 23.2 | 73.1 | 93.1 | 99.3 |
| 15 | Pre (85) | Labrafil (5) | Carbopol 971P NF (10) | Ranitidine HCl | 20.6 | 58.4 | 82.1 | 89.4 |
| 16 | Pre (85) | Labrafil (5) | Blanose (10) | Paracetamol | 15.4 | 53.2 | 84.2 | 90.7 |
| 17 | Pre (85) | Labrafil (5) | Carmellose Sodium (10) | Paracetamol | 17.4 | 48.3 | 86.5 | 97.4 |
| 18 | Stearic acid (80) | Labrafil (5) | Collidon CL (15) | Paracetamol | 25.3 | 73.3 | 92 | 96.7 |
| 19 | Stearic acid (80) | Labrafil (10) | Sodium chloride (fine grade) (10) | Paracetamol | 10.9 | 28.9 | 64.4 | 72.1 |
| 20 | Stearic acid (75) | PEG 6000 (15) | Mannitol (fine grade) (10) | Paracetamol | 12.4 | 35.8 | 68.9 | 74.3 |
| 21 | Pre (70) | PEG 6000 (15) | micronised Lactose (15) | Paracetamol | 13.5 | 42.1 | 79.6 | 92.3 |
| 22 | Pre (75) | PEG 6000 (15) | Potassium hydrogen carbonate (10) | Paracetamol | 54.3 | 89.3 | 96.8 | 99.7 |
| 23 | Pre (75) | PEG 6000 (15) | Potassium hydrogen carbonate (10) | Caffeine | 63.5 | 84.3 | 96.9 | 101.3 |
| 24 | Pre (75) | Labrafil (5) | Amb (10), CaCO3 (10) | Caffeine | 15.3 | 67.9 | 95.3 | 98.6 |
| 25 | Pre (80) | Labrafil (5) | CaCO3 (5) + micronised Lactose (10) | Caffeine | 23.4 | 93.4 | 100.8 | 102.8 |
| 26 | Stearic acid (80) | Labrafil (5) | Collidon CL (15) | Caffeine | 19.6 | 67.7 | 85.6 | 96.7 |
| 27 | Stearic acid (80) | PEG 6000 (10) | Blanose (10) | Caffeine | 17.4 | 60.3 | 82.7 | 93.5 |
| 28 | Pre (75) | Labrafil (5) | Blanose (10) + potassium hydrogen carbonate (10) | Ranitidine HCl | 17.9 | 84.6 | 98.8 | 99.6 |
| 29 | Pre (85) | Cr A6 (5) | Polyox (10) | Ranitidine HCl | 2.01 | 24.13 | 51.28 | 78.46 |
| 30 | Pre (75) | Labrafil (5) | Polyox (20) | Ranitidine HCl | 3.83 | 20.41 | 41.23 | 66.2 |
| 31 | Stearic acid (75) | Labrafil (5) | Amb (20) | Ranitidine HCl | 35.5 | 74.2 | 89 | 94.1 |

EXAMPLE 6

In this example the embodiment of the present invention is exemplified in which the release compound or a part of the release compound is applied as a subcoat between the core containing the active ingredient and the taste-masking coat. The process was carried out in the same equipment as described in example 1 and essentially the same coating proceedings were used. The process was adapted and first a subcoat of the release compound was sprayed onto the core and then the taste-masking layer was sprayed onto the sub-coated intermediate product. The composition of the layers and the relative amount of the components of the layers as well as the active ingredient are summarized in the table below.

Following the protocol of example 4, the dissolution of the active ingredient was measured and the results are also summarized in the following table.

| Sample No. | taste masking component | surfactant or other substance in taste masking coating | Release compound | active ingredient | percent active ingredient dissolution | | | |
|---|---|---|---|---|---|---|---|---|
| | | | | | 5 min | 15 min | 30 min | 60 min |
| 32 | Pre (75) | PEG 4000 (25) | Subcoat 5% Carbopol (based on starting material Paracetamol) | Paracetamol | 19.08 | 50.59 | 78.61 | 94.79 |
| 33 | Pre (75) | PEG 4000 (25) | Subcoat 3% Carbopol (based on starting material Paracetamol) | Paracetamol | 43.08 | 84.2 | 97.86 | 101.18 |
| 34 | Pre (70) | PEG 4000 (25) | Amb (5) in taste masking coating; Subcoat 5% Carbopol (based on starting material Paracetamol) | Paracetamol | 22.09 | 53.49 | 79.03 | 93.6 |
| 35 | Pre (75) | PEG 4000 (25) | Subcoat 3% Carbopol (based on starting material Paracetamol) | Ranitidine HCl | 43.08 | 84.2 | 97.86 | 101.18 |

The invention claimed is:

1. A process for producing a solid, coated fast-release pharmaceutical composition, said process comprising the steps of:
   (i) providing a core containing one or more pharmaceutically active ingredients and optionally one or more pharmaceutically acceptable excipients,
   (ii) providing at least one coating composition comprising at least one taste-masking compound having a melting point of at least 40° C. and an HLB value of 10 or less, wherein the at least one coating composition comprising the taste-masking compound is heated to a temperature of at least 40° C. so that the taste-masking compound is in melt phase,
   (iii) providing at least one release compound that, in the gastrointestinal tract, either causes disruption or disintegration of the taste-masking layer or improves the permeability of the taste-masking layer for the one or more pharmaceutically active ingredients, and
   (iv) spray-coating the core of step (i) with the at least one coating composition of step (ii) and the release compound of step (iii) to yield a solid, coated fast-release pharmaceutical composition having a dissolution profile measured according to the European Pharmacopoeia in a USP type 2 paddle apparatus at 75 rpm in 900 ml aqueous buffer at 37° C. for 30 minutes under acidic conditions (pH=1) and then under conditions at which the active ingredients are soluble, wherein after 45 minutes at least 60% of the one or more active ingredients is dissolved,
   wherein the taste-masking compound is present in the at least one coating composition of step (ii) in an amount in the range of 70% to 95%, based on the weight of the coating composition, and
   wherein the release compound is present in the at least one coating composition of step (ii) or in a seperate coating composition in an amount in the range of 5% to 30%, based on the weight of the respective coating composition.

2. The process according to claim 1, wherein the at least one coating composition comprising the at least one taste-masking compound also contains the at least one release compound.

3. The process according to claim 1, wherein two different coating compositions are sprayed onto the core, one coating composition comprising the at least one taste-masking compound and the other coating composition comprising the at least one release compound.

4. The process according to claim 3, wherein the coating composition comprising the at least one release compound is sprayed onto the core as a powder.

5. The process according to claim 3, wherein the two coating compositions are sprayed simultaneously onto the core to provide a taste-masking layer which also contains at least one release compound.

6. The process according to claim 3, further comprising a first coating step wherein a coating composition comprising at least one release compound is sprayed onto the core to provide a layer with the release compound and a second coating step wherein a coating composition comprising the at least one taste-masking compound is sprayed onto the core containing the layer with the at least one release compound.

7. The process according to claim 6, wherein the coating composition comprising the at least one taste-masking compound contains in addition at least one release compound.

8. The process according to claim 1, wherein the taste-masking compound is selected from the group consisting of fatty acids, fatty alcohols, fatty acid triglycerides, fatty acid partial glycerides, fatty alcohol-PEG-ethers, fatty alcohol-PEG-esters, fatty acid esters and fatty acid polyglycerols.

9. The process according to claim 8, wherein the taste-masking compound is selected from the group consisting of stearic acid, polyethylene glycol saturated polyglycolyzed glycerides, glycerol palmitostearate and glycerol behenate.

10. The process according to claim 1, wherein the release compound is selected from the group consisting of compounds that react under acidic conditions, swelling agents, inorganic salts, organic compounds and hydrophilic polymers that are soluble in aqueous media, and mixtures thereof.

11. The process according to claim 1, wherein the at least one taste-masking compound has a melting point in the range of 50 to 80° C.

12. The process according to claim 1, wherein the release compound is selected from the group consisting of carbonic acid salts, polyacrylic exchange resins and mixtures thereof.

13. The process according to claim 1, wherein the coating composition comprising the at least one release compound and/or the at least one taste-masking compound also contains at least one additional compound selected from the group of surfactants, polyethylene glycols, glycerol and propylene glycol.

14. The process according to claim 13, wherein the surfactant is selected from the group consisting of sorbitane fatty acid esters, polyethylene alkyl ethers, polyoxyethylene castor oil derivatives, polyoxyethylene sorbitane fatty acid esters, polyoxyethylene stearates and polyoxyethylene-polyoxypropylene-copolymers.

15. The process according to claim 13, wherein the additional compound is present in an amount of up to 35%, based on the weight of the coating composition.

16. The process according to claim 1, wherein the pharmaceutically active ingredient is selected from the group consisting of ranitidine, famotidine, cimitidine, caffeine, paracetamol, acetyl salicylic acid (ASA), cetirizine, loratadine, diphenhydramine, gauifenisin, ibuprofen, ketoprofen, naproxen, acemetacin, pseudoephedrine, phenylephrine, dextromethorphane, calcium acetate, zinc sulfate, zinc fumarate, and zinc and iron salts.

17. A solid coated fast-release pharmaceutical composition obtained according to the process of claim 1, said composition having a dissolution profile measured according to the European Pharmacopoeia in a USP type 2 paddle apparatus at 75 rpm in 900 ml aqueous buffer at 37° C. for 30 minutes under acidic conditions (pH=1) and then under conditions at which the active ingredients are soluble, wherein after 45 minutes at least 60% of the one or more active ingredients is dissolved.

18. The solid coated pharmaceutical composition according to claim 17, wherein the release compound is a compound which reacts under acidic conditions and wherein the pharmaceutical composition has a dissolution profile measured according to the European Pharmacopoeia in a USP type 2 paddle apparatus at 75 rpm in 900 ml aqueous buffer at 37° C. for 30 minutes under acidic conditions (pH=1) and then under conditions at which the active ingredients are soluble, wherein at least 60% of the one or more active ingredients is dissolved after 30 minutes.

19. The solid coated pharmaceutical composition according to claim 17, wherein the release compound is selected from among an inorganic salt, an organic compound, and a hydrophilic polymer that is soluble in aqueous media.

* * * * *